United States Patent [19]

Ruud

[11] Patent Number: 4,686,631
[45] Date of Patent: Aug. 11, 1987

[54] METHOD FOR DETERMINING INTERNAL STRESSES IN POLYCRYSTALLINE SOLIDS

[76] Inventor: Clayton O. Ruud, 310 Toftrees Ave., #135, State College, Pa. 16803

[21] Appl. No.: 699,992

[22] Filed: Feb. 8, 1985

[51] Int. Cl.$^4$ .................. G01C 25/00; G01N 23/20; G01B 5/30
[52] U.S. Cl. .................. 364/508; 364/571; 378/72; 378/78; 73/760; 73/787
[58] Field of Search .................. 364/508, 555, 571; 378/71, 72, 78, 81; 73/760, 786, 787; 250/307; 356/31

[56] References Cited

U.S. PATENT DOCUMENTS

| | | | |
|---|---|---|---|
| 3,617,705 | 11/1971 | Takano et al. | 378/72 |
| 4,042,825 | 8/1971 | Ruud | 378/72 |
| 4,095,103 | 6/1978 | Cohen et al. | 378/72 |
| 4,128,762 | 12/1978 | Nagao et al. | 378/72 |
| 4,195,349 | 3/1980 | Balkanli | 364/571 |
| 4,223,388 | 9/1980 | Nishikawa | 364/571 X |
| 4,288,852 | 9/1981 | Holland | 364/508 X |
| 4,337,517 | 6/1982 | Nickel et al. | 364/571 |
| 4,399,515 | 8/1983 | Gross | 364/557 X |
| 4,426,718 | 1/1984 | Hayashi et al. | 378/72 |
| 4,489,425 | 12/1984 | Borgonovi | 364/508 X |
| 4,561,062 | 12/1985 | Mitchell | 364/508 X |

*Primary Examiner*—Errol A. Krass
*Assistant Examiner*—Joseph L. Dixon
*Attorney, Agent, or Firm*—Thomas J. Greer, Jr.

[57] ABSTRACT

Previous methods for determining internal stress in polycrystalline solids by X-ray diffraction techniques have required that the distance between the X-ray irradiated surface of the sample under investigation and the X-ray detection surface for the diffracted X-rays be known. According to the practice of this invention, stress measurement can be made without determining the sample to detector distance as a separate step. Two or more sets of detection surfaces, i.e., X-ray detector channels, are arranged around the incident X-ray beam, usually on opposite sides of the cone of diffracted X-rays from one another. The invention employs a calibration procedure which provides a set of calibration parameters, which, when used with X-ray stress equations, yields accurate internal stress measurement without the prior art requirement of determining the sample to detector distance.

12 Claims, 5 Drawing Figures

METHOD FOR DETERMINING INTERNAL STRESSES IN POLYCRYSTALLINE SOLIDS

PRIOR ART STATEMENT

The inventor knows of the following prior art germane to this invention as set forth in the following U.S. Pat. Nos.:
4,095,103
3,402,291
3,517,194
2,386,785
3,483,377
4,042,825
3,011,060
3,717,705
3,126,479
3,934,138

BACKGROUND OF THE INVENTION

The determination and analysis of internal (residual) stresses in crystalline solids is an old and well-known art. In essence, the diffraction of X-rays directed at the surface of the material being analyzed comprises the analytical tool by means of which the spacing between adjacent internal atomic planes is determined. This information is collected in the form of diffracted intensity and position data which, in turn, provides the analyst with what is needed to determine internal stresses.

More specifically, the so-called "Bragg Relation" expressed as $$n\lambda = 2d \sin\theta$$

where
 n = 1, 2, ..., i.e., any integer
 $\lambda$ = wavelength of the diffracted radiation
 d = interplanar spacing
 $\theta$ = Bragg angle is employed to determine the position and intensity of the diffracted X-ray beam impinging upon the surface of the solid crystalline substance. In those applications where the interplanar spacing (d) is known, either $\lambda$ or $\theta$ is known. From the practical standpoint, when using either polycrystalline or powdered materials, $\lambda$ becomes a constant and $2\theta$ is a measured angle. In measuring the latter, however, the diffracted X-ray beam undergoes some diffusion and, therefore, is spread out over a range of from a few tenths to several degrees. This necessitates, of course, ascertaining a mean diffraction angle $2\theta$, and such is accomplished by taking intensity measurements at several angular positions.

The prior art includes several different ways of measuring the intensity and position of the diffracted X-ray beam, four such methods being quite widely used. They comprise the following:
 1. Scanning Goniometer (Diffractometer)
 2. Film Camera
 3. Electro-Optical Combinations
 4. Position Sensitive Proportional Counters The first of these, namely, the scanning goniometer, consists basically of a mechanical turntable upon which the sample can be mounted and oriented at a selected angular position ($\theta$) with respect to an incident X-ray beam and at double the chosen angle ($2\theta$) with respect to a suitable detector such that the latter is in a position to intercept the diffracted beam. Details concerning the construction and operation of the aforesaid apparatus can be found in any one of the following references:
 1. Barrett, C. S., *Structure of Metals*, 2nd Ed., McGraw-Hill, N.Y., 1952.
 2. Cullity, B. D., *X-Ray Diffraction*, Addison-Wesley, Reading, Mass., 1956

While the scanning goniometer still constitutes one of the most widely used instruments for determining the position and intensity of a diffracted X-ray beam, it suffers from many shortcomings, not the least of which is its bulk and excessive time per measurement. Moreover, it requires an extremely stable power supply along with complex and highly sophisticated auxiliary instrumentation. Last but by no means least is the fact that it is quite complicated to use and requires service at periodic intervals to keep it operating satisfactorily.

Cameras of one type or another are also used to record both the position and intensity of the diffracted X-ray beam. Certain of these cameras are described in the literature references already listed. While less expensive, simpler and easier to use than the scanning goniometer, most of the cameras developed for this purpose suffer from the inherent disadvantages of being both slow and inaccurate in a field where speed and accuracy are highly desirable.

The remaining two methods used to position and measure the intensity of a diffracted X-ray beam, namely, the electro-optical devices and the conventionally used position-sensitive proportional counters, share the problems of the goniometer in that, while they provide accurate measurements in a reasonably short time, they are both bulky and require mechanical movement to provide internal stress measurement, as well as calling for precise control of the specimen to detector distance. Even so, aside from the device described herein, such methods represent the highest state of the art. A detailed description of the various electro-optical methods presently employed in the location and measurement of the intensity of the diffracted X-ray beam can be found in Green, R. E., "Electro-Optical Systems for Dynamic Display of X-Ray Diffraction Images," *Advances in X-Ray Analysis*, Vol. 14, Plenum Press, N.Y., 1971. Similarly, an informative description of the position-sensitive proportional counters can be found in James, M. R. and J. B. Cohen, The Application of a Position-Sensitive X-Ray Detector to the Measurement of Residual Stresses," *Advances in X-Ray Analysis*, Vol. 19, Kendall/Hunt Publishing Co., Dubuque, Iowa, 1976, and in U.S. Pat. No. 4,095,103.

From the foregoing, it should be apparent that the ideal combination of method and instrument for determining the internal (residual) stress in polycrystalline solids via diffracted X-ray beams must, first of all, be fast and accurate. Consistent with the above, it should be easy to use and, preferably, portable. While cost is always a factor of some considerable importance, it may be outweighed by others such as, for example, the elimination of the need for complex and expensive auxiliary equipment and fixtures for applying the instrument (apparatus).

It has now been found in accordance with the teaching of this invention that the shortcomings of the prior art methods and apparatus can, in fact, be overcome while, at the same time, providing the sought-after speed and accuracy contained in a highly portable piece of equipment. Not only is the method combined with a suitable instrument accurate, it is easy for relatively untrained technicians to learn to use. Further, its unique feature of tolerance for variation of the sample to the X-ray sensitive detector surface distance, which is not present in any other similar type of combination of method and instrument, provides for unprecedented speed and convenience of application, without the need of special fixtures or measurement devices.

Accordingly, it is the principal object of the present invention to provide a novel method to calibrate and apply a novel and improved device of the electro-optical, proportional or solid state type, of position-sensitive diffractometers for ascertaining the precise angle of a diffracted X-ray beam while allowing broad tolerances in the sample-to-detector distance.

Another object of this invention is to provide a novel method for use with an electro-optical or proportional types of diffractometers which allows broad tolerances in the distance between the detector and the sample to be measured.

Another object of the invention herein disclosed and claimed is to provide a method for determining the interplanar spacing in a solid crystalline sample that reduces the need for auxiliary apparatus, fixturing, and instrumentation to a near-minimum level.

Yet another objective is to provide an improved method by which the user can quickly ascertain both accurate and reliable data concerning the mean diffraction angle $2\theta$ in the Bragg Relation, while allowing broad tolerances in the sample-to-detector distance.

Further objects are to provide methods that an instrument of the class described can be simple to operate, easy to learn to use, compact, free of frequent alignment problems, and one that is readily adaptable for use in most of the common X-ray diffraction applications.

Other objects will be in part apparent and in part pointed out specifically hereinafter in connection with the description of the drawings that follow, and in which.

Figure 1:
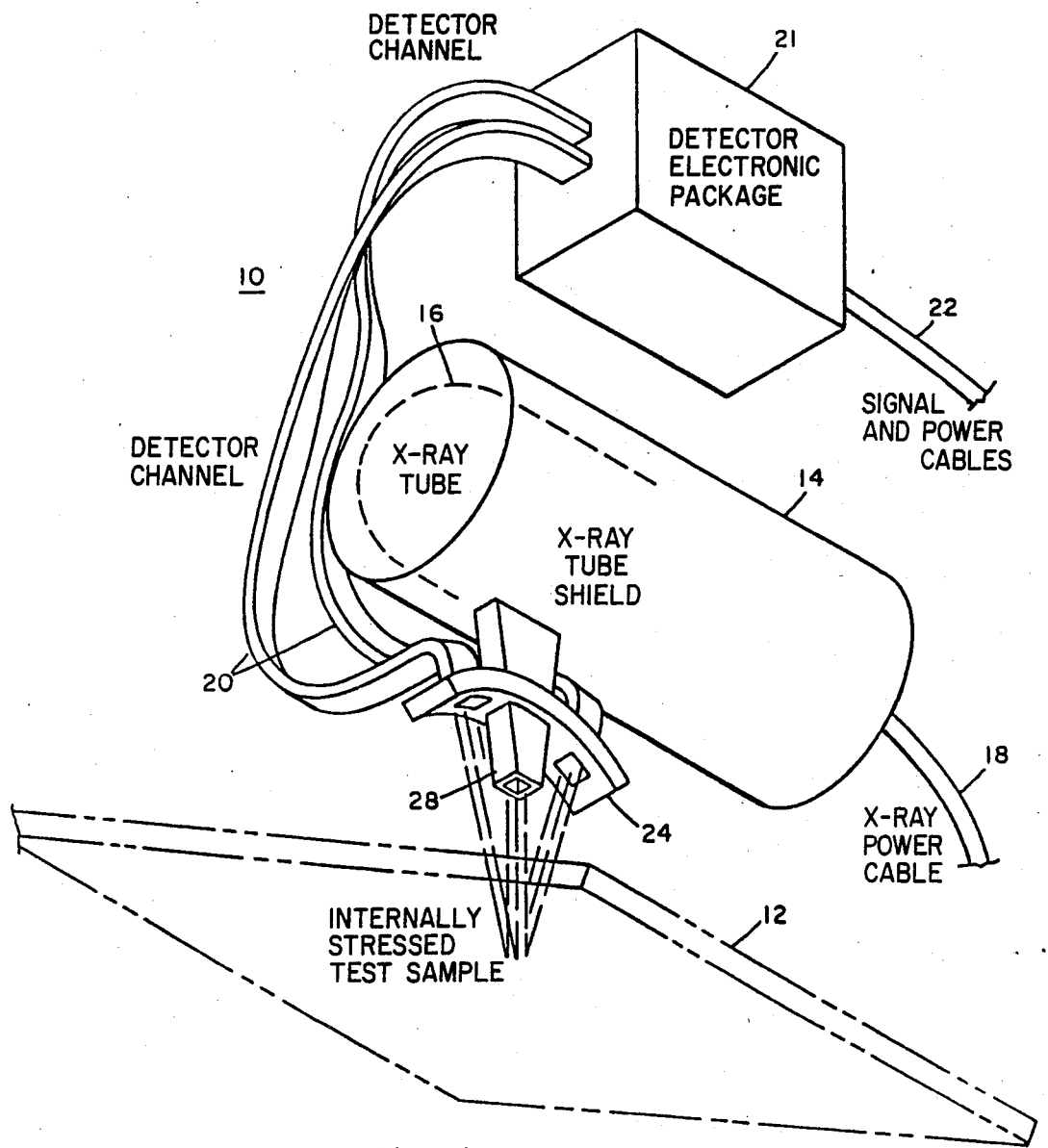
FIG. 1 is a schematic view of the probe of an apparatus suitable for applying the method; showing it in relation to the sample.

Referring next to the drawings for a detailed description of the present invention and a suitable position-sensitive diffractometer for its application, reference numeral 10 has been selected to identify in a general way the head or probe portion of the apparatus while numeral 12 refers to the surface of the sample to be tested. A tubular X-ray tube shield 14 of conventional design houses an X-ray tube 16 which is, in turn, connected to a suitable power supply (not shown) by X-ray power cables 18 that enter the case at the end opposite that upon which the X-ray sensitive surfaces of the detector channel sets 20 are attached. Other insulated power cables 22 supply power to the detector electronic subassemblies 21, in the probe 10 along with other electronic components thereof that will be identified and described in detail presently. An apparatus to position the X-ray sensitive surfaces, in this example a fiber optic holder is shown as 24. Also, an incident X-ray beam collimator is shown as 28. Components 28 and 24 are interfaced into the X-ray tube shield 14.

The head, or probe, 10 is the most important feature of a suitable position-sensitive diffractometer unit and, as will be seen in FIGS. 2 and 3 to which detailed reference will now be made, it includes, among other things in one example of a suitable unit, two fiber optic channel bundle sets 30A and 30B each of which is made up of many individual fibers arranged in coherent relation such that a given fiber occupies precisely the same position at the input face I as it does at the output face K on the opposite end thereof. The size of the individual fibers is, of course, a function of what degree of image resolution is desired and this, in turn, depends upon the resolving power of the scintillation phosphor coating 32 on the input faces of the bundles, the electronic scanners and other elements of the head subassembly. For instance, if the phosphor coating 32 the input faces of the fiber bundles 30A and 30B has a spacial resolution of only about 30 microns, then any fiber having a diameter equal to or less than $30\mu$ will have no adverse effect upon the quality of the transmitted beam. Fiber optic bundles 30A and 30B made up of 10 $\mu$ fibers are readily obtainable and they exceed the resolving capabilities of other elements of the head subassembly.

From the standpoint of the phosphor coating 32 it must, of course, respond to the ionizing radiation in the form of the reflected X-ray beam falling thereon by emitting light photons. Those phosphors capable of the most efficient conversion of the ionizing radiation to visible light, unfortunately, also scatter the light the most and, therefore, have poor spacial resolution. Thus, the selection of a suitable phosphor and its physical characteristics on the face of the fiber optic bundles, i.e., thick layer or thin, etc., largely becomes a trade-off between the desired resolution and energy conversion efficiency. From a practical standpoint, it has been found z that a phosphor having approximately a 30 $\mu$ spacial resolution and 10% energy conversion efficiency works quite well. While these are the prime considerations, the phosphor chosen should, in addition, remain stable over long periods of time and under varying climatic conditions. Also of prime importance is the transmissibility of the visible light because it is not enough to emit the light if the phosphor will not transmit it the fiber optic channel bundles 30A and 30B.

Next, detailed reference will be made to the diagram of FIG. 3 in which certain important relationships have been revealed. The size of the input surface I of each fiber optic channel bundle 30A or 30B controls the range of allowed distances separating this surface from the surface of the sample (or specimen) 12, i.e., the so-called "$R_o$" distance in the diagram. It is the tolerance for this distance that provides a unique feature of this invention. Obviously, the longer this surface is, the greater the distance and broader the range can be of $R_o$.

Figure 3:
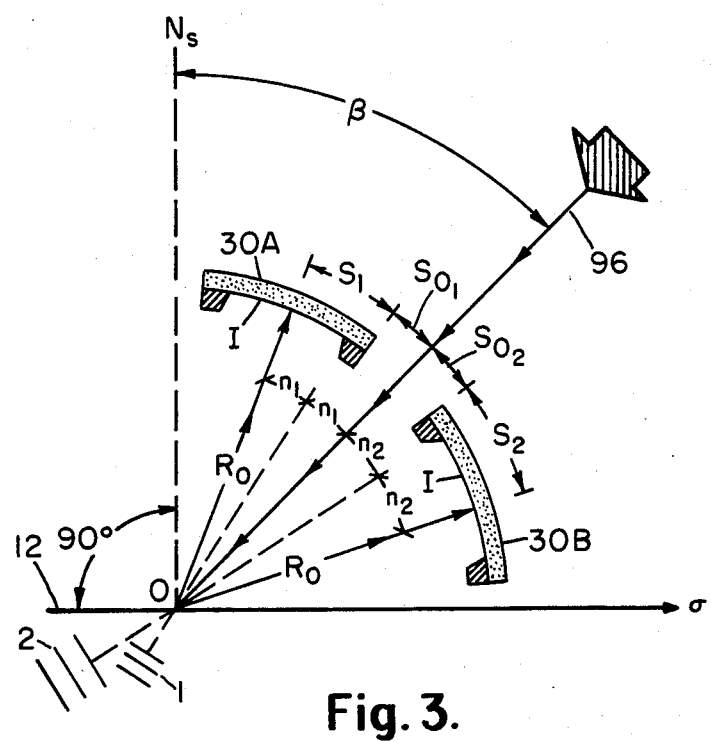
FIG. 3 is a diagram illustrating certain critical angular and spacial relationships which must be either known or measured in order to determine the residual stresses present in a sample by means of the most simple procedure wherein the positions occupied by the two beams of reflected radiation are located at the same time.

The spacing between the two channel or bundles 30A and 30B is, likewise, an important consideration and one that is determined from the angular relationships revealed in FIG. 3. In X-ray stress measurement applications, it is the angle $2\eta$ on each side of the incident X-ray beam together with the desired specimen-to-detector surface distance $R_o$ that determine the proper spacing between bundles 30A and 30B. It can be shown, for example, that if the system is ultimately capable of producing a 60 μ final spacial resolution, $R_o$ is selected to be 1.6 inches, and $2\theta \simeq 156°$ ($2\theta = 2\theta_1 = 2\theta_2 = 180 - 156° = 24°$), for Cr K-alpha radiation and a powdered aluminum specimen, then a spacing of about 1.0 inches center to center of the optic bundle surfaces I will be optimum. A spacing such as this will accommodate a $2\theta$ angular resolution of 0.08°. Moreover, this same spacing would accommodate ferritic or martensitic steel or iron spaced ($R_o$) 1.6 inches from the detector surface also having a $2\theta$ of 156° using CrK radiation. Other metals and ceramics may, of course, require a different spacing between bundles 30A and 30B in order to achieve optimum conditions; however, as above noted, once the values for $R_o$, $2\eta$, and the X-radiation wavelength are known, this distance can be easily calculated. For a powdered, i.e., zero residual stress specimen, $2\eta = 2\eta_1 = 2\eta_2$.

A length of the input surfaces I of the fiber optic detectors 30A and 30B of one-half inch for each such surface has proven to be entirely adequate for application of the method. In width, one-tenth of an inch has, likewise, been proven satisfactory.

The tilt of these input surfaces I is also important and, ideally, they should conform to the circle whose radius is $R_o$, as shown in FIG. 3.

o When this relationship is present, optimum resolution of the reflected beam is insured. However, flat rather than curved input surfaces I, see FIG. 2, have been shown to provide adequate results when using the calibration and application method which is an integral part of this invention.

Finally, with regard to the length of the fibers relative to those in the same bundle or those in the other bundle, it does not appear to make any difference that they are not the same other than, perhaps, a negligible loss in intensity in the longer fibers due to the fact that the light has to travel a slightly greater distance.

Returning again to FIG. 2, it can be seen in this example of a suitable position sensitive detector that the output ends K of the fiber optic channel sets are joined to the face of an image intensifier 34 in essentially side-by-side parallel relation. This intensifier has no other function than that of increasing the intensity of the image appearing at the output end of the detector bundles to a level where it can be read by a scanner subassembly and photo diode array within a reasonable length of time, the latter subassembly having been designated broadly by reference numeral 36.

In FIG. 3, numeral 96 indicates the path of the X-ray beam projected from the X-ray beam collimator 28 and striking the surface of sample 12. The X-ray beam 96 is positioned at an angle β to the normal $N_s$ surface of the sample 12. Fiber optic bundle sets 30A and 30B are positioned at a distance $R_o$ from intersection of the surface of sample 12 and the X-ray beam 96 and are adapted to receive X-ray beams from the surface of the sample 12.

Other designations set forth in FIG. 3 are more fully described in the foregoing specification.

Figure 4:
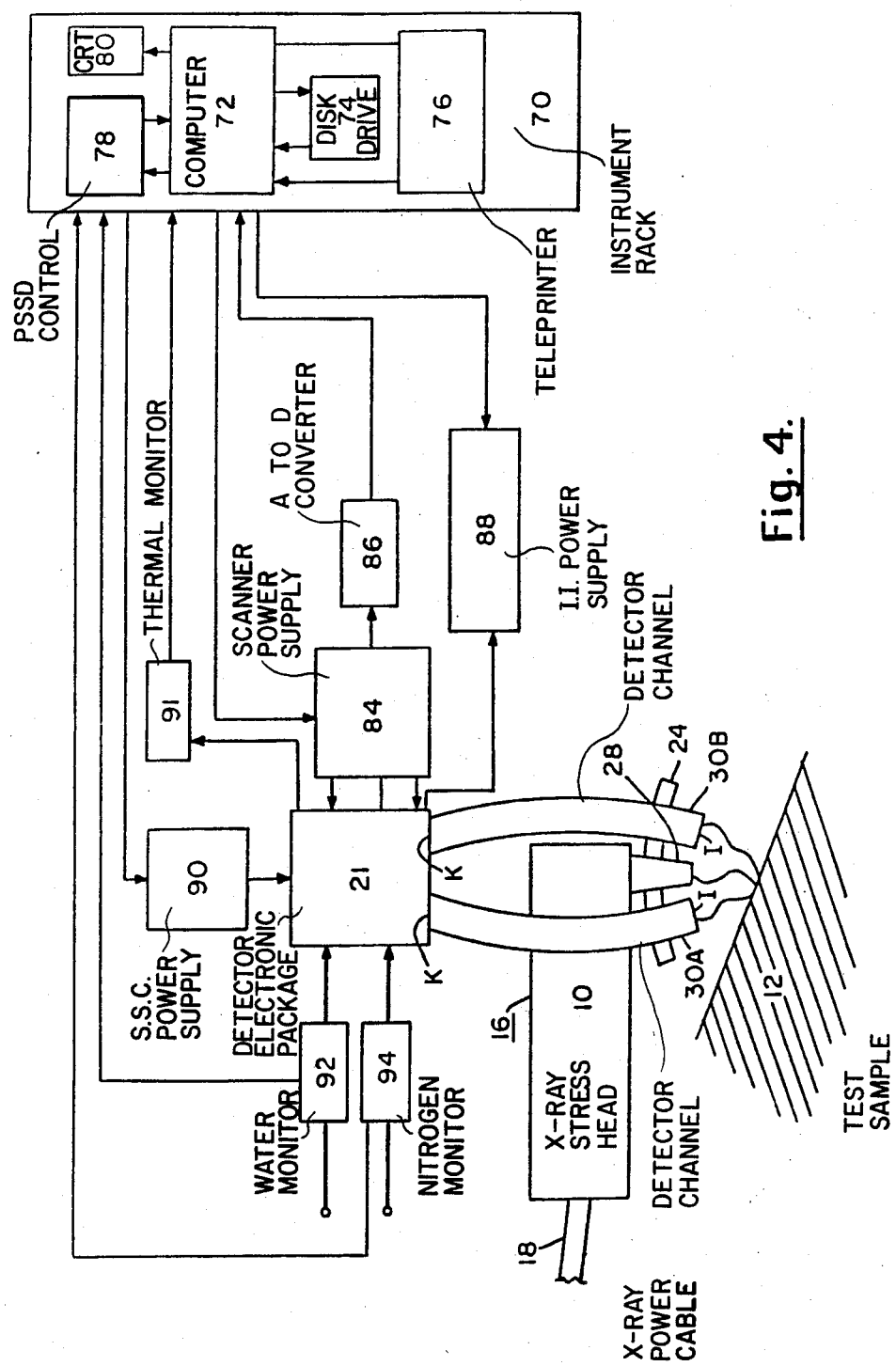
FIG. 4 is a block diagram showing the components of the position sensitive scintillation detector including its connections with a computer and other related elements.

Referring to FIG. 4, an instrument rack 70 contains a computer 72 connected to a dual floppy disc drive 74 and to a computer teleprinter 76. The computer 72 is also connected to a position sensitive scintillation detector control panel 78 and to a CRT 80 located in rack 70.

Figure 2:
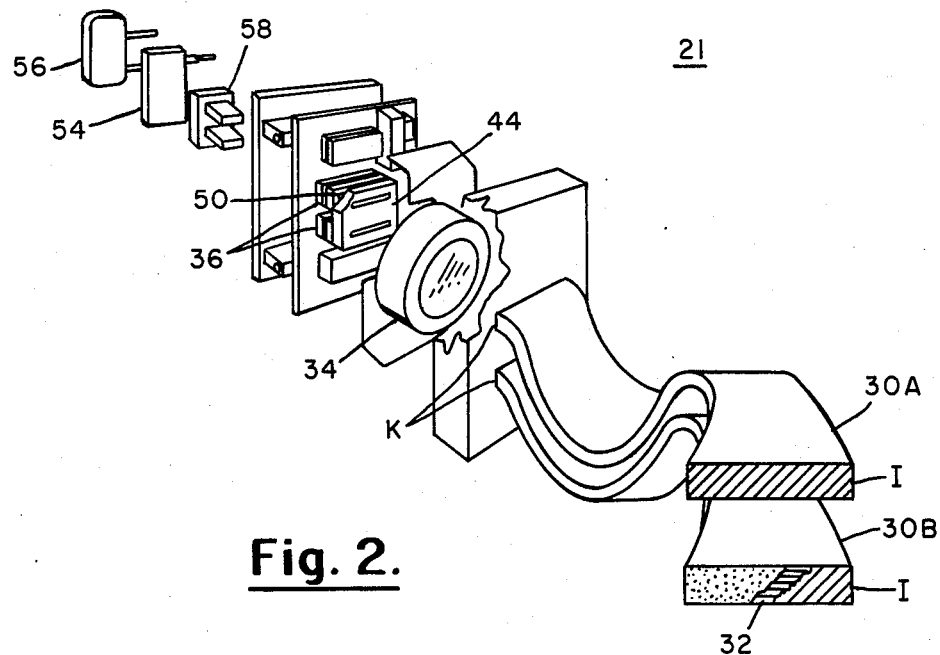
FIG. 2 is an exploded perspective view of an electronic package of the FIG. 1 probe but to a somewhat larger scale, certain portions having again been broken away to better reveal the interior construction.

The electronic package 21 of FIG. 2, also referred to as electronics cube 21 is connected to a diode array scanner and power supply 84 which in turn is coupled to the computer 72 through an AID converter 86. The diode array scanner and power supply 84 is also directly connected to the computer 72. Thermal monitor 91 is connected between the electronic package 21 and computer 72. The electronic package 21 is coupled to the computer 72 through an image intensifier power supply 88. Likewise the electronic package 21 is connected to the control panel 78 through a solid state cooler power supply 90. The control panel 78 is then coupled to a water monitor 92 which controls a cooling water supplied to the electronic package 21. Likewise the control panel 78 is connected to a nitrogen monitor 94 which controls the nitrogen supplied to the electronic package 21. The nitrogen circuit is not needed when the electronic package 21 is hermetically sealed. The fiber optics channel bundle sets 30A and 30B and related components extend from the electronic package 21 in a manner set forth in FIGS. 1 and 2 and previously described.

Even after the analogue of the X-ray pattern has been intensified, it still is not visible to the naked eye. In fact, it must accumulate photons for several fractions of seconds to seconds in order to produce usable data.

More than one type of intensifier is available for this purpose, however, only the proximity focused type containing a multi-channel solid state electron multiplier is small enough and sufficiently lightweight to answer the needs of a portable unit. Of equal importance is the fact that such units utilize hollow fibers which are much more compatible with the fiber optic channel bundles 30A and 30B than other types which employ either electrostatic or magnetic focusing of the image in that the transition from fiber optics in the detector to a non-fiber intensifier results in considerable inefficiency at the interface therebetween. On the other hand, by going from a fiber detector to a fiber-type intensifier, these losses are minimized thus producing a usable image on the output screen at the rear of the intensifier in the shortest time interval with the least gain.

While no novelty is predicated upon the image intensifier 34 per se, it consists of an input photocathode positioned to mate with the output surfaces K of the detector o channel bundles 30A and 30B and take the dim signal therefrom. This photocathode then delivers the image thus received to a multichannel plate consisting of hollow fibers filled with a solid state material capable of producing electron multiplication. Approximately 2–300 volts are applied between the photocathode and the input to the multi-channel plate for the purpose of inducing the electrons to leave the photocathode and enter the latter. The voltage impressed across plate is generally made variable and usually runs somewhere between 4–800 volts. This is sufficient to produce an electron gain of about 1 to $10^4$. The voltage between the plate and screen, on the other hand, is generally around 5 KV which is effective to accelerate the electrons efficiently to produce a visible image.

Behind the image intensifier 34 lies a mask 44 containing apertures filled with fiber optic windows that register with the analogue signal appearing on the output screen of the image intensifier 34 and also with photodiode arrays 36 therebehind. These windows cooperate to transfer the image on the screen to the photodiode arrays 36 with minimal transmission losses in much the same way that the fibers in multi-channel plate do with respect to the image picked up by the latter at photocathode. It has been found that windows made of quartz or optical glass (lenses) severely reduce the intensity of the transmitted image. For this reason, it is important that the fiber optic bundle be used as a light transmission medium throughout the system in order that a detectable signal be produced in a short time interval, 60 seconds or less, and with minimal amplification. The window-forming fiber optic bundles are, in essence, just short segments of the detector bundles as they perform similar functions and are subject to the same design parameters, i.e., be of a diameter no greater than that of the maximum spacial resolution of the phosphor, etc.

Photodiode arrays 36 constitute a part of a scanner subassembly 50 which, like intensifier 34, is a commercially available item except that it has been modified as previously mentioned to replace the usual quartz windows with the fiber optic ones. A typical array has some 512 photodiodes arranged in side by side linear relation. Often the analogue signal is very weak thus necessitating a long data accumulation period (several seconds), the scanner must be cooled to reduce the leakage current. Accordingly, the scanner is cooled by a small thermoelectric cooler 54 of standard design and a water cooled heat exchanger 56. Even without the use of refrigerants, the foregoing cooling system has proven adequate to maintain the scanner at a temperature some 40° C. below ambient which is more than enough to allow photon collection for 60 seconds or more.

In FIG. 2, reference numeral 58 designates a conduction member which cooperates with the thermoelectric cooler 54 against which it lies to maintain the necessary scanner temperature. Other types of cooling systems may, of course, be substituted for the one illustrated provided only that they do not interfere or otherwise detract from the portability of the probe and the various electrical and coolant lines assocated therewith.

The scanner 36 also includes a shift register which samples each of the 512 photodiodes sequentially in accordance with an input clock rate. A typical one used is a "RETICON" Model RL 512C/17 solid state scanner which processes the information picked up by the detector with which it is operatively associated and delivers same as an output signal for video display. No attempt has been made to include either the scanner circuitry or any details concerning the equipment used to evaluate the output signal.

Finally, a typical version of a suitable apparatus will be seen to include a computer 72 and certain peripherals as set forth in FIG. 4. In operation the X-ray beam leaves the X-ray tube 16, in FIG. 1, and impinges upon the sample or specimen 12 after having been passed through a suitable aperture in the X-ray beam collimator 28, the design and construction of which are well within the skill of the art.

The specimen 12 is placed a fixed approximate distance from the input surfaces I of the fiber bundles 30A and 30B in FIG. 2. The knowledge of this distance is important to the measurement of stresses; however, it can be determined by the novel method described herein when the apparatus is properly calibrated. The method for this calibration is a vital part of the invention and is described subsequently. By properly tilting the specimen with respect to the incident X-ray beam and the input surfaces of the bundles 30, the latter surfaces will be in a position to receive the reflection off the crystal planes of the specimen such that the internal (residual) stress in the specimen can be determined.

In the example of a suitable position sensitive diffractometer described the output ends K of the bundles deliver their respective dim images to the image intensifier 34 as before where it is amplified, scanned, read, and delivered to the computer 72 which computes the stress using the Bragg relationship and the calibration parameters, as well as certain material constants. Once again, in this example of a suitable instrument, fiber optics are used throughout the image transmission chain to minimize the interface losses and, most important, to get the information in a readable form as quickly as possible.

The improved method for ascertaining the unknown angle $2\theta$ in the Bragg relation is also unique in that the X-ray sensitive surface of the detector channel sets are placed an approximate instead of a precise distance away from the specimen and in a position to intercept said diffracted beam. The X-ray sensitive surfaces in the example apparatus are preferably oriented in right angular relation to the diffracted beam, and the fibers of the bundle should be essentially parallel thereto for best results. The fiber optic bundle is employed as a signal transfer mechanism by means of which the analogue signal (image) of the X-rays impinging upon the phosphor is reproduced at a remote location. The visible light image thus reproduced must be intensified in accordance with presently available technology in order to make it possible for the image to be scanned and analyzed within a reasonably short time frame. In so doing, it is important to use an image intensifier 34 employing the same type of image transfer mechanism as the detector, namely, a fiber optic bundle, as opposed to traditional optical systems and the like. The same is true of the windows transmitting the image thus intensified to the electronic scanning array. Ordinarily, quartz windows are used to this purpose; however, in accordance with the teaching of the instant method, fiber optic windows are substituted therefore.

In the scanning step used by the example apparatus for application of the method, the intensified visible light image (analogue signal) is repeatedly scanned electronically and converted to an electrical image wherein the magnitude of the electrical output from an array of solid state sensors is proportional to the intensity of the visible light received by said sensor. This electrical image is then analyzed and used as the basis for an output which, when combined with the calibration information described subsequently, provides the analyst with precise information on the location of the diffracted X-ray beam relative to the incident one impinging upon the sample.

STRESS MEASUREMENT TECHNIQUES

The primary application of the previously described apparatus and this method invention is to measure residual stresses in polycrystalline materials. Therefore, an explanation of techniques for stress measurement by X-ray diffraction must be provided. There are three basic techniques for measuring stresses based on the X-ray diffraction method. These are the double-exposure or two-angle technique (DET); the single-exposure or one-angle technique (SET); and the sin-square-psi or multi-angle technique ($\sin^2\Psi$). The angle of exposure which is referred to is that between the incident X-ray beam and the specimen surface normal, i.e., beta ($\beta$) in FIG. 3. The following paragraphs briefly discuss each of the three techniques; more detail may be found in the reference, SAE, "Residual Stress Measurement by X-Ray Diffraction - SAE J784a," Soc. of Auto. Eng. Inc., Warrendale, PA.

DOUBLE-EXPOSURE TECHNIQUE (DET)

The double-exposure technique (DET) measures the interatomic spacing (d) of planes at two different attitudes ($\Psi 1$ and $\Psi 2$) with the specimen surface. One set of planes are usually those which are parallel to the surface, and thus the psi angle is zero, i.e., $\Psi_1 = 0°$. The second set of planes are those that make a reasonably steep angle with the surface, e.g., $\Psi_2 = 45°$ or $60°$. These angles are often chosen because their $\sin^2\Psi$ values are 0.50 and 0.75, and this simplifies calculation. The DET has been the most commonly used technique and has been applied to film and diffractometer measurement. However, its application presents the opportunity for the introduction of large errors due to specimen to detector distance variations when the stress measuring head is moved from one $\Psi$ angle to another on any instrument except a conventional goniometer based diffractometer. It has mainly been applied because most conventional instrumentation is incapable of measuring two $\Psi$ angles simultaneously. The combination of method and suitable instrument described herein is uniquely capable of applying the DET in a portable instrument without the introduction of the error mentioned.

SINGLE-EXPOSURE TECHNIQUE (SET)

In order to measure residual stress, the diffracting angle ($\theta$) from the same type of crystallographic planes at two different angles with respect to the surface need to be measured (see FIG. 3). This is possible to accomplish with a single incident X-ray beam angle because X-rays are diffracted by a fine-grained polycrystalline surface as a cone of beams. By measuring the Bragg angle ($\theta$) on two opposite sides of the cone, stress can be measured using a single beta ($\beta$) angle (see FIG. 3). Note that the diffracted beams are measured in a plane which is normal to the cone axis, i.e. the incident X-ray beam. also, that the two positions of measurement on the approximate circle produced by the intersection of the cone of X-rays and the aforementioned plane are the closest and farthest away, i.e., opposite sides of the circumference, from the specimen surface normal. Actually, when beta ($\beta$) is not equal to zero, the plane-cone intersection forms a circle only when the metal is unstressed. In a stressed metal the circle is deformed into a skewed ellipse and $\eta_1 \neq \eta_2$.

Then as described in the previous paragraph, a single incident angle ($\beta$) can be used to provide readings at two psi ($\Psi$) angles using the equation $$\sigma = \frac{E[(R-L) + (S_{o2} - S_{o1})]}{(1+\nu) 4R_o \sin^2\theta_o \sin 2\beta} \quad (1)$$

where E is the Elastic Constant (Young's Modulus), $\nu$ is the Poisson's Ratio, and the rest of the parameters are defined in FIG. 3, where $L=S_2$ and $R=S_l$. The major parametric difference between the single- and double-exposure techniques is that one psi ($\Psi$) angle is usually equal to zero degrees for the double-exposure technique. The combination of method and suitable instrument described herein is unique in its ability to efficiently perform the SET, as well as the DET and $\sin^2\Psi$. Further it is unique in providing for application of the SET without the need of incorporating added steps in the stress measurement procedure to precisely measure or control the sample-to-detector distance for each individual stress measurement.

SIN-SQUARE-PSI TECHNIQUE ($SIN^2\Psi$)

This technique uses the fact that in stressed, untextured (i.e., no crystallographic preferred orientation) metals and ceramics the interplanar atomic spacings (d) of crystallographic equivalent planes (i.e., identical miller indices, hkl) will vary consistently with their psi ($\Psi$) angle. Furthermore, a plot of this d space versus sin-square-psi will produce a straight line.

In order to calculate stress from such a plot, the data must be plotted as ($d_{105}-d_o$, i.e., interplanar spacing at some angle psi ($\Psi$) minus the spacing of the unstressed metal divided by the spacing of the unstressed metal. From this plot the stress in the surface is obtained by multiplying the slope of the line by $E/(1+\nu)$. Also, the sum of the two principal stresses ($\sigma_1 + \sigma_2$) in the surface may be obtained from the intercept, $\epsilon$ or $\Delta d/d_o$, at psi equals zero ($\Psi = 0$). Details for accomplishing these calculations may be found in the SAE reference previously cited. The method and suitable apparatus described herein is unique in its application of the sin-square-psi technique in that careful control and/or measurement of th sample-to-detector distance is circumvented.

APPLICATION OF STRESS MEASUREMENT

A unique method and suitable apparatus capable of applying all of the techniques of X-ray stress measurement more proficiently than heretofore ever possible has been discussed previously in this document. For the most rapid application the information about the diffracted X-ray beams on each side of the incident X-ray beam can then be used by the computer used with the position-sensitive diffractometer described as a suitable device herein to determine the internal mechanical stress in the irradiated portion of the specimen by using a single incident angle ($\beta$) to provide readings at two angles, using equation 1.

It must be recognized that for precise adherence to the X-ray stress measurement single-exposure technique geometry shown in FIG. 3, the left and right X-ray sensitive surfaces of the fiber optics channel bundles 30A and 30B must be tangent to the circle upon which the detectors lie. Note that the planar fiber optic surfaces in FIG. 2 take the place of the curved film in FIG. 3. Furthermore, these two fiber optic surfaces must be tangent at their exact center and exactly the same distance from the incident X-ray beam. In order to accommodate these conditions as nearly as possible, a precision circular track of the fiber optics holder 24 FIG. 1 is provided that is attached to the incident beam collimator 28. This fiber optic track provides an extremely stable base for mounting the fiber optics. The latter are mechanically held rigidly in retainers which are slid along the inside track of the holder, and when properly located are secured in position by a number of set screws. However, in spite of this precise hardware, the extreme alignment tolerances of less than $\pm 0.0001$ inches ($\pm 0.002$ mm) cannot reasonably be met by conventional fabrication techniques. Therefore, to account for the error in location of the center of the X-ray sensitive fiber optics a correction is incorporated into the stress calculation algorithm based on equation 1. The parameters for this correction are derived from a calibration procedure which is an integral part of this invention and determines experimentally the relative misalignment of the left and right fiber optic with respect to each other. In other words, a parabolid regression is used to fit experimental data to the equation $$R = A \cdot L^2 + B \cdot L + C, \quad (2)$$

where R and L are the location of the right and left peaks ($S_1$ and $S_2$ in FIG. 3), and A, B, and C are the constants for the empirically determined parabola. These constants are used in the equation as a substitution for the term $S_{o2} - S_{o1}$ in equation 1, where $$S_{o2} - S_{o1} = AL^2 + BL + C - L. \quad (3)$$

The operational procedure for determining A, B, and C is described subsequently and is an integral part of this patent. A linear equation in place of the parabolic equation (2) has also been found to be applicable in some cases. Thus other polynomials may be useful.

If the constants are not correct, changes in $R_o$, the distance between the specimen and stress head, will cause apparent changes in the measured stress. This can be tested by using a powder coupon standard or some other known stress standard at a predetermined $\beta$ angle and moving the head up or down to give a few percent difference in $R_o$ and is a method of calibration confirmation.

There are two major errors caused by non-focusing conditions inherent in all techniques of X-ray stress measurement, including the single-exposure technique (SET). One is due to the uncertainty of the detector circle to specimen distance, $R_o$, in FIG. 3, and it is corrected in the method of this invention through its iterative calculation with respect to stress. The other is due to the need to use a beta ($\beta$) angle other than zero; it is ameliorated through application of a Lorentz-Polarization and absorption correction (LPA) which is a well-known procedure.

The iterative calculation of $R_o$ which is an integral part of this invention uses the following equation for the first estimation of $R_o$, $$R_{o(1)} = \frac{L + R + S_{o1} + S_{o2}}{2 \tan 2\eta_o}, \quad (4)$$

where L and R are the first estimate of the X-ray peak positions, $S_{o2} + S_{o1} = 2 \times (Ideal\ R_o) \sin 2\eta_o - (L+R)_{R_o=Ideal}$, $\eta_o = 90 - \theta_o$, $\theta_o =$ Bragg angle for the unstressed metal. For all iterations beyond the first, i.e., n+1, the calculation $$R_{o(n+1)} = \frac{L + R + S_{o1} + S_{o2}}{2 \tan 2\eta_o} - \frac{L_{RERR} + R_{RERR}}{2 \tan 2\eta_o} \quad (5)$$

is used to determine $R_o$, where $$L_{RERR} = \frac{2\sigma_{(n)} R_{o(n)}}{(E/1 + v) \cot \theta_o} \sin^2 \psi_L; \quad (6)$$

$$R_{RERR} = \frac{2\sigma_{(n)} R_{o(n)}}{(E/1 + v) \cot \theta_o} \sin^2 \psi_R, \quad (7)$$

with all terms previously defined, except $\Psi_L = \beta - \eta_L$ and $\Psi_R = \beta - \eta_R$, where $\eta_L = \frac{1}{2} Arctan\ [(L+S_{o1})/R_o(n)]$ and $\eta_R = \frac{1}{2} Arctan[(R-S_{o2})/R_{o(n)}]$. In other words, the estimation of the variable $R_o$ is revised by a more accurate estimation of $\sigma$ at each n+1 iteration. This is continued until the $R_o$ is consistent from one iteration to the next by predetermined error allowance.

It is more accurate, rapid, and convenient to determine $R_o$ by this novel means rather than to carefully measure or control it to the ideal $R_o$ by some optical or mechanical method. The successive $R_o$ terms are also used to calculate the $\theta_L$ and $\theta_R$ angles used in the LPA correction where $\theta_L = 90 - \eta_L$ and $\theta_R = 90 - \eta_R$.

The calculation of the terms used for the LPA correction is based upon the equation $$LPA = \frac{1}{2} \left( \frac{1 + \cos^2 2\theta_i}{\sin^2 \theta_i} \right) + \frac{1}{2} (1 - \tan \psi_i \cot \theta_i). \quad (8)$$

$\theta_i = \theta_L$ or $\theta_R$
$\psi_i = \psi_L$ or $\psi_R$

The rationale and need for this equation is described in the SAE reference previously cited.

The equations presented herein serve only to provide a description of the processes used by a computer in the use of the method of simultaneous $R_o$ and stress determination which is a part of this invention.

CALIBRATION METHOD

The purpose of this method is to generate five (5) parameters which are necessary for the application of this method invention. These parameters are the calibration coefficients designated A, 5, and C, average left and right peak positions at the ideal $R_o$. Their relevance has been explained previously. The first three parameters provide $(S_{o2} - S_{o1})$, where $$S_{o2} - S_{o1} = AL^2 + BL + C - L$$

and the last $$S_{o2} + S_{o1} = (Ideal\ R_o) \times 2 \tan \eta_o - (L+R)_{R_o} = Ideal \quad (9)$$

In the $(S_{o2} + S_{o1})$ relation, $\eta_o = 90 - \theta_o$, where $\theta_o$, is the Bragg angle of an unstressed metal or ceramic and (L+R) is the sum of the apexes of the diffracted peaks at $R_o$=Ideal. $S_{o1}$ and $S_{o2}$, shown in FIG. 3, can be calculated from these relations, and this is an important condition in providing the unique feature of sample-to-detector distance tolerance of this method.

The procedure for obtaining A, B, C, and $(S_{o1} + S_{o2})$ involves the use of a specimen that is known to have a constant stress over the area irradiated by the X-ray beam. It is prudent to select a loose powder of a polycrystalline material of as nearly the same composition as the material in which residual stresses are to eventually be measured. The powder is packed in a shallow well such that it has a planar surface. Standard X-ray diffractometer powder specimen holders are quite suitable and the technique of packing is well known. This powder is then placed so that the incident X-ray beam strikes its surface at 90°; at the ideal $R_o$ distance around which the operator desires to work. Several pairs of X-ray data (L and R) are obtained at this ideal $R_o$ and the $S_1$ and $S_2$ (L and R) values recorded. The $R_o$ is then lengthened; for example, 3% and more data is taken. This is repeated at three more distances approximately equivalent to, e.g., $R_o+6\%$ $R_o-3\%$, and $R_o-6\%$. These data are then used to calculate A, B, and C through a mathematical regression solution procedure which is well known.

The average L and R reading at the ideal $R_o$ is used as $S_{o1} + S_{o2}$.

APPLICATION OF PARAMETERS

In order to provide accurate residual stress measurement with the method and suitable position-sensitive diffractometer previously described, the following steps are followed.

1. The calibration parameters A, B, C, and $(S_{o1}+S_{o2})$-$R_o = Ideal$; the known value of the crystallographic and elastic/constants for the specimen metal or ceramic; and the angle $\beta$ are read into the dedicated computer provided with a suitable stress measuring apparatus.

2. The X-rays are placed incident upon a polycrystalline specimen of unknown stress with the incident beam at an angle $\beta$ to the specimen surface normal.

3. The detector is then interrogated and the computer determines the X-ray peak position from each channel set using state-of-the-art X-ray peak fitting and location algorithms.

4. With the position of the peaks $S_1$ and $S_2$ (L and R) established, the procedure then used by the computer for determination of accurate $R_o$ and $\sigma$ (stress) is iterative and as follows, assuming that Lorentz-polarization and absorption (LPA) errors are accounted for when necessary. In the first iteration $R_o$ is estimated from $S_1$ and $S_2$ (where $S_1 = L$ and $S_2 = R$) by $R_{o(n=1)}$ = First iterative estimation of $R_o$ $$R_{o(n=1)} = \frac{L + R + (S_{o1} + S_{o2})}{2 \sin 2\eta_o},$$

where $2\eta_o = 180 - 2\theta_o$. The first estimates of $\sigma$, i.e., $\sigma_{(n=1)}$ is obtained by $$\sigma_{(n=1)} = \frac{E}{(1+\nu)} \frac{(R-L) - (L - AL^2 - BL - C)}{4R_{\sigma(n=1)} \sin^2\theta_o \sin 2\beta}. \quad (11)$$

Then for all iterations greater than $n=1$, $R_o$ is established by $$R_{o(n>1)} = \frac{L + R + (S_{o1} + S_{o2})}{2 \sin 2\eta_o} - \frac{L_{RERR} + R_{RERR}}{2 \sin 2\eta_o}, \quad (12)$$

where $$L_{RERR} = \frac{2\sigma_{(n-1)} R_{o(n-1)}}{\cot \theta_o (E/1+\nu)} \sin^2 \psi_L \quad (13)$$

$$R_{RERR} = \frac{2\sigma_{(n-1)} R_{o(n-1)}}{\cot \theta_o (E/1+\nu)} \sin^2 \psi_R, \quad (14)$$

where $$\psi_L = \beta - \tfrac{1}{2} \arctan\left(\frac{S_{o1} + L}{R_{o(n-1)}}\right) \quad (15)$$

$$\psi_R = \beta - \tfrac{1}{2} \arctan\left(\frac{S_{o2} + R}{R_{o(n-1)}}\right) \quad (16)$$

and $\sigma_{(n>1)}$ is obtained by $$\sigma_{(n)} = \frac{E}{(1+\nu)} \frac{(R-L) - (L - AL^2 - BL - C)}{4R_{o(n)} \sin^2\theta_o \sin 2\beta}. \quad (17)$$

Iterations are continued until $(\sigma_n - \sigma_{n-1}) \div \sigma_n$ is reduced to an error tolerance established by the operator, e.g., 0.01.

This computational procedure provides unprecedently accurate $\sigma$, $R_o$, $\Psi_L$, $\Psi_R$, $d_L$, $d_R$, $\theta_L$, $\theta_R \sin^2\Psi_L$, and $\sin^2\Psi_R$, values without the necessity of precise control of $R_o$. Note that $\theta_L = 90 - \beta + \Psi_L$ and $\theta_R = 90 - \Psi_R + \beta$. The interplanar spacing, d, of the planes contributing to $\theta_L$ and $\theta_R$ are $d_L = \lambda/2 \sin\theta_L$ and $d_R = \lambda/2 \sin\theta_R$ from the Bragg equation ($n\lambda = 2d \sin\theta$, where $n = 1$, $\lambda =$ wavelength of the X-radiation used). Note n is the Bragg relation is not the same as the subscript n in the previous equations.

TYPICAL EXAMPLES OF ADJUSTMENT, CALIBRATION, CONFIRMATION, AND STRESS MEASUREMENT PROCEDURES

An unprecedently rapid, precise, and convenient method for determining the internal strain (residual stress) in polycrystalline metallic and ceramic components is described in two examples which follow. However, preceding these example descriptions is the following introduction.

INTRODUCTION

A typical procedure includes the adjusting of the position and attitude of the scintillation phosphor-coated ends of the fiber optics of the example position-sensitive diffractometer to the line of the incident X-ray beam and the detector circle, described by the radius $R_o$ in FIG. 3. After this adjustment has been performed to accommodate the crystallographic parameters of the polycrystalline samples in which stresses are to be subsequently measured to the satisfaction of the operator, the calibration coefficients (A, B, and C in equation 9) are obtained, which allows the algorithm, which is a part of the method of application described herein, to correct for errors of adjustment too precise for the operator to be expected to eliminate through mechanical adjustment. These errors include:

1. Imprecision in location of the detector surfaces (I in FIG. 3) such that the line of the incident beam bisects the distance between them.

2. Imprecision in location of the detector surfaces, such that an X-ray beam diffracted at precisely $2n_1$ or $2n_2$ (see FIG. 3) at the preselected $R_o$ distance is centered on the detector surfaces (I in FIG. 3).

3. Imprecision in location of the detector surfaces s that their linear center is exactly tangent to the detector circle described by the pre-selected $R_o$; or imprecision in location of circular curved detector surfaces so that their circle coincides with the circumference of the detector circle described by the pre-selected $R_o$; or some other imprecise alignment of another shape of detector surfaces of a configuration for applied x-ray optics.

After the calibration, which provides the coefficients A, B, and C and the precise location of the x-ray peaks on either detector at the preselected distance, $R_o$, is established (i.e., L and R at the ideal $R_o$), the accuracy of the calibration is confirmed.

Finally, the calibrated apparatus is applied to internal stress measurement of a crystalline solid. The unique feature of the calibration combined with a position-sensitive diffractometer with at least two detector channel sets, that is not present in any other similar processes, is that the distance between the specimen and detector surfaces need no be precisely controlled or measured in order to provide precise residual stress readings.

EXAMPLE 1

The first specific example will be for internal (including residual) stress measurement in ferritic or martensitic steel. The crystalline parameters of a very large range of useful iron base alloys are sufficiently similar that a single calibration procedure of the apparatus, which is an important part of this patent, will provide the coefficients necessary for accurate stress measurement for nearly all ferritic and martensitic steels. These alloys may be generically grouped into the category of ferritic and martensitic steels, but not austenitic stainless steels.

For the following description the following is assumed. The X-ray sensitive surfaces are planar and rectangular, as depicted as 3OA and 3OB in FIG. 2. The cross-sectional length of the fiber optic channel bundle, i.e., 3OA and 3OB in FIG. 2, and also the X-ray sensitive scintillation phosphor coating is 0.5 inches (12.7 mm). This dimension represents the length of the linear position sensitive detector. Chromium K-alpha characteristic-X-radiation is to be used to diffract from the (311) crystallographic planes of the iron base crystal lattice. This diffraction occurs nominally at a Bragg angle of about 78 degrees. It has been found in practice that a convenient specimen-to-detector circle radius, see $R_o$ in FIG. 3, is about 1.57 inches (40 mm), i.e., the pre-selected $R_o=1.57$ inches (40 mm). However, distances as great as 2.4 inches (60 mm) and as small as 1.2 inches (30 mm) have been used, and larger and shorter distances than these are also feasible.

1.1 ADJUSTMENT

The X-ray sensitive ends of the detector surfaces, e.g., the fiber optic bundles (3OA and 3OB in FIG. 2) of the example instrument are typically contained in collars which have circular tabs, approximately parallel, or tangent, to the long dimension of the fiber optic cross-section. These tabs are of a circular radius so that they slide into two weys in the fiber optic holder (24 in FIG. 1). Thus, the fiber optic collars, and therefore the X-ray sensitive portion of the detector channel sets 3OA and 3OB, can be moved along the fiber optic holder arc while approximately maintaining the detector surfaces at the pre-selected $R_o$. Thereby, the distance between the line of the incident X-ray beam and the detector channel sets 3OA and 3OB can be varied to provide different angles between a normal at the center of the fiber optic end and the incident beam, i.e., $2\eta_1$ and $2\eta_2$ in FIG. 3 can be varied. For this example, i.e., ferritic and martensitic steels, this adjustment would be performed to provide $2\eta_1=2\eta_2=180-156°$, where 156° is twice the nominal Bragg angle for the steels, i.e., $2\times 78°$. Thus, with the $R_o=1.57$ inches (40 mm) the arc distance between the center line of the incident X-ray beam and the center of each fiber optic sensing surface (3OA and 3OB in FIG. 2) would be $2\pi R_o (24/360)=0.65$ inches (17 mm).

STEP 1: Therefore, $S_1+S_{o1}$ and $S_2+S_{o2}$ in FIG. 3 would be adjusted to about 0.65 inches (17 mm).

This would constitute the only adjustment needed to prepare the stress-measuring apparatus for internal stress measurements in ferritic and martensitic steels.

1.2 DETERMINATION OF CALIBRATION COEFFICIENTS

STEP 2: The stress-measuring apparatus shown in FIG. 1 is next positioned with respect to a calibration specimen such that the incident X-ray beam emitting from the collimator (28 in FIG. 1) strikes the specimen at a normal angle.

The calibration specimen is selected such that it has nearly the same crystallographic spacing as the steel and has a uniform stress field in the volume irradiated by the X-ray beam. It has been found that the most convenient choice for such a specimen for steel is a fine (−400 mesh) iron powder. This powder has been previously poured into a holder such that a planar surface several times larger than the irradiated area could be conveniently molded. It is this planar surface to which the incident X-ray beam is placed normal.

STEP 3: The distance between the X-ray detector surfaces and center of the irradiated area is next adjusted to $R_o=1.57\pm 0.01$ inches ($40\pm 0.2$ mm) using a template gage.

STEP 4: The X-ray detector and X-ray source are then activated and five readings of $S_1$ and $S_2$ (FIG. 3) are made, and provided by the dedicated computer, at the selected distance of $R_o=1.57$ inches (40 mm).

STEP 5: The $R_o$ is next increased about 0.05 inches (1.3 mm) and five more readings obtained.

STEP 6: The $R_o$ is increased another 0.05 inches (1.3 mm) and five more readings obtained.

STEP 7: The $R_o$ is decreased about 0.15 inches (3.8 mm) and five more readings obtained.

STEP 8: The $R_o$ is decreased about 0.05 inches (1.3 mm) and five more readings obtained.

Note: At any $R_o$ other than that of 1.57 inches (40 mm), the irradiated area on the specimen is not at the center of the fiber optic holder arc circle. In these non ideal (i.e., $R_o \neq 1.57$ inches) $R_o$ distances, $R_o$ is usually measured as the distance from the intersection of the arc and the incident X-ray beam to the irradiated specimen surface (see FIG. 3). Also, it must be recognized that there are a number of constraints on the span of $R_o$ which can be used with a given detector size, i.e., length of fiber optic cross-section (3OA and 3OB in FIG. 2). Rule of thumb figures are that the $R_o$ should be $3.0\pm 0.5$ times the length of the fiber optic cross-section and the span of $R_o$ should not exceed 12% of $R_o$.

The computer interfaced to the X-ray detector apparatus described herein therefore provides groups of five $S_1$ and $S_2$ (see FIG. 3) values for each $R_o$ distance used through Steps 4 through 8.

STEP 9: These then are fit to a polynomial equation, $S_2 = AS^2_1 + BS_1 + C$, and the parameters A, B, and C calculated by a regression process. Also, the average $S_1$ and $S_2$ at the ideal $R_o$, i.e., $R_o=1.57$ inches (40 mm) is calculated to provide the information to calculate $S_{o2}+S_{o1}$.

For this example of calibration for steel, the coefficients determined were $A=0.67074\times 10^{-9}$ inches$^2$, $B=0.96771\times 10^{-3}$ inches, $C=3.3739$, and at $R_o=1.57$ inches (40 mm) the average $S_1=L=0.25677$ inches and average $S_2=R=0.25567$ inches.

1.3 CONFIRMATION

In order to ascertain if the calibration coefficients determined are adequate for the internal stress measurement to be undertaken, a confirmation test is conducted. This is done by placing a fine, loose powder of iron, with a planar surface, such that the incident beam can be made incident upon it. A loose powder is selected because such a specimen is incapable of supporting a macro stress between its grains and thus is a known, zero, stress specimen.

STEP 10: The X-ray stress measuring apparatus is arranged such that the incident X-ray beam strikes the powder specimen at some angle beta (see $\beta$ in FIG. 3) to the normal of the surface of the specimen. For steel a beta angle of 30° has been found to be convenient and to provide good precision and accuracy.

STEP 11: The $R_o$ distance between the center of the irradiated spot on the specimen and the detector is then adjusted to be roughly 1.57 inches (40 mm) and the detector and X-ray source is activated.

STEP 12: The necessary crystallographic, elastic, and geometric parameters for steel, as well as the five calibration coefficients, are read into the computer; the X-rays are activated; and the computer prompted to determine the stress ($\sigma$) and $R_o$ distance (see equations 5 and 14). Three readings are usually made at the first $R_o$ distance, i.e., about 1.57 inches.

STEP 13: The $R_o$ is next increased about 0.04 inches (1 mm) and three more readings are made.

STEP 14: The $R_o$ is again increased about 0.04 inches (1 mm) and three more readings are made.

STEP 15: The $R_o$ is next decreased about 0.12 inches (3 mm) and three more readings are made.

STEP 16: The $R_o$ is next decreased about 0.04 inches (1 mm) and three more readings are made.

Thus, fifteen readings have been taken which span $R_o$ distances from about 1.49 inches (38 mm) to about 1.65 inches (42 mm), i.e., the range in which the operator expects to be measuring stresses in steel, and the mean and standard deviation of all fifteen readings were $-0.6$ KSI (4 Mpa)$\pm 0.9$ KSI (6 Mpa). The X-ray information for each reading of the set of three, at each distance of $R_o$, eas obtained in six seconds, with a standard X-ray source, an unprecedented short time for collection of such information. The tolerance for variation in specimen-to-detector distance, i.e., the parameter designated $R_o$ herein, is unprecedented. The ability to tolerate such variations and provide good accuracy (i.e., $-0.6$ KSI compared with the true stress of zero) and precision (i.e., 0.9 KSI) in a very short time is a unique feature not present in any other similar combination of apparatus and procedure.

1.4 STRESS MEASUREMENT

With the stress measurement apparatus adjusted and calibrated, and with the quality of the calibration confirmed, internal (including residual) stress measurements on martensitic and ferritic steel components can now be performed.

STEP 17: In this example the X-ray stress head shown in FIG. 1 was positioned over a large alloy steel weldment and the attitude of the head was adjusted so that the angle $\beta$ in FIG. 3 was 30°.

STEP 18: The distance between the stress head and weldment, i.e., $R_o$, was then approximately set between 1.49 and 1.65 inches (38 and 42 mm).

STEP 19: The X-ray source was activated and the computer was prompted to determine the residual stress ($\sigma$) and $R_o$. Note: it was not necessary to read the crystallographic, elastic, and geometric parameters for steel, as well as the calibration coefficients into the computer since that had previously been done during the confirmation. The resultant stress was 33.4 KSI (235 MPa) compressive and the $R_o$ was 1.59 inches (40.3 mm).

Stress measurements were continued for the rest of the day resulting in several hundred readings from the weldment with residual stresses ranging from 34.7 KSI (244 MPa) compression to 27.5 KSI (194 MPa) tensile and $R_o$ ranging from 1.50 to 1.63 inches (38.2 to 41.5 mm).

EXAMPLE 2

The second specific example will be for internal (including residual stress measurement in copper and alpha copper alloys. The crystalline parameters of a very large range of useful copper base alloys are sufficiently similar that a single calibration procedure of the apparatus, which is an important part of this patent, will provide the coefficients necessary for accurate stress measurement for them.

For the following description the following is assumed. The X-ray sensitive surfaces are planar and rectangular, as depicted as 30A and 30B in FIG. 2. The cross-sectional length of the fiber optic bundle, i.e., 30A and 30B in FIG. 2, and also the X-ray sensitive scintillation phosphor coating is 0.5 inches (12.7 mm). This dimension represents the length of the linear position sensitive detector. Copper K-alpha characteristic X-radiation is to be used to diffract from the (420) crystallographic plane of the copper base crystal lattice. This diffraction occurs nominally at a Bragg angle of about 73 degrees. As noted in the first example it has been found in practice that a convenient specimen-to-detector circle radius, see $R_o$ in FIG. 3, is about 1.57 inches (40 mm), i.e., the pre-selected $R_o=1.57$ inches (40 mm).

2.1 ADJUSTMENT

For this example, i.e., copper and alpha copper alloys, the adjustment of the detector channel sets would be performed to provide $2\eta_1=2\eta_2=180-146°$, where 146° is twice the nominal Bragg angle for pure copper, i.e., $2 \times 73°$. Thus, with the $R_o=1.57$ inches (40 mm) the arc distance between the center line of the incident X-ray beam and the center of each fiber optic sensing surface (30A and 30B in FIG. 2) would be $2\pi R_o (34°/361°)=0.93$ inches (24 mm).

STEP 1: Therefore, $S_1+S_{o1}$ and $S_2+S_{o2}$ in FIG. 3 would be adjusted to about 0.93 inches (24 mm).

This would constitute the only adjustment needed to prepare the stress-measuring apparatus for internal stress measurements in copper and alpha copper alloys.

2.2 DETERMINATION OF CALIBRATION COEFFICIENTS

STEP 2: The stress-measuring apparatus shown in FIG. 1 is next positioned with respect to a calibration specimen such that the incident -X-ray beam emitting from the collimator (28 in FIG. 1) strikes the specimen at a normal angle.

The calibration specimen is selected such that it has nearly the same crystallographic spacing as the copper and alpha copper alloys and has a uniform stress field in the volume irradiated by the X-ray beam. It has been found that the most convenient choice for such a specimen for copper is a fine ($-400$ mesh) pure copper powder. This powder has been previously poured into a holder such that a planar surface several times larger than the irradiated area could be conveniently molded.

It is this planar surface to which the incident X-ray beam is placed normal.

STEP 3: The distance between the X-ray detector surfaces and center of the irradiated area is next adjusted to $R_o=1.57\pm0.01$ inches ($40\pm0.2$ mm) using a template gage.

STEP 4: The X-ray detector and X-ray source are then activated and five readings of $S_1$ and $S_2$ (FIG. 3) are made, and provided by the dedicated computer, at the selected distance of $R_o=1.57$ inches (40 mm).

STEP 5: The $R_o$ is next increased about 0.06 inches (1.5 mm) and five more readings obtained.

STEP 6: The $R_o$ is increased another 0.06 inches (1.5 mm) and five more readings obtained.

STEP 7: The $R_o$ is decreased about 0.18 inches (4.5 mm) and five more readings obtained.

STEP 8: The $R_o$ is decreased about 0.06 inches (1.5 mm) and five more readings obtained.

Note: At any $R_o$ other than that of 1.57 inches (40 mm), the irradiated area on the specimen is not at the center of the fiber optic holder arc circle. In these non-ideal (i.e., $R_o \neq 1.57$ inches) $R_o$ distances, $R_o$ is usually measured as the distance from the intersection of the arc and the incident X-ray beam to the irradiated specimen surface (see FIG. 3).

The computer interfaced to the X-ray detector apparatus described herein therefore provides groups of five $S_1$ and $S_2$ (see FIG. 3) values for each $R_o$ distance used through Steps 4 through 8.

STEP 9: These then are fit to a polynomial equation, $S_2=AS^2_1+BS_1+C$, and the parameters A, B, and C calculated by a regression process. Also, the average $S_1$ and $S_2$ at the ideal $R_o$, i.e., $R_o=1.57$ inches (40 mm) is calculated to provide the information to calculate $S_{o2}+S_{o1}$.

For this example of calibration for copper and alpha copper alloys, the coefficients determined were $A=1.12508\times10^{-9}$ inches$^2$, $B=0.40751\times10^{-3}$ inches, $C=79.4304$, and at $R_o=1.57$ inches (40 mm) the average $S_1=L=0.25495$ inches and average $S_2=R=0.25643$ inches.

2.3 CONFIRMATION

In order to ascertain if the calibration coefficients determine are adequate for the internal stress measurement to be undertaken, a confirmation test is conducted. This is done by placing a fine, loose powder of copper, with a planar surface, such that the incident beam can be made incident upon it. A loose powder is selected because such a specimen is incapable of supporting a macro stress between its grains and thus is a known, zero, stress specimen.

STEP 10: The X-ray stress measuring apparatus is arranged such tha the incident X-ray beam strikes the powder specimen at some angle beta (see $\beta$ in FIG. 3) to the normal of the surface of the specimen. For copper and alpha copper alloys a beta angle of 25° has been found to be convenient and to provide good precision and accuracy.

STEP 11: The $R_o$ distance between the center of the irradiated spot on the specimen and the detector is then adjusted to be roughly 1.57 inches (40 mm) and the detector and X-ray source is activated.

STEP 12: The necessary crystallographic, elastic, and geometric parameters for copper, as well as the five calibration coefficients, are read into the computer; the X-rays are activated; and the computer prompted to determine the stress ($\sigma$) and $R_o$ distance (see equations 5 and 14). Three readings are usually made at the first $R_o$ distance, i.e., about 1.57 inches.

STEP 13: The $R_o$ is next increased about 0.05 inches (1.3 mm) and three more readings are made.

STEP 14: The $R_o$ is again increased about 0.05 inches (1.3 mm) and three more readings are made.

STEP 15: The $R_o$ is next decreased about 0.15 inches (3.8 mm) and three more readings are made.

STEP 16: The $R_o$ is next decreased about 0.05 inches (1.3 mm) and three more readings are made.

Thus, fifteen readings have been taken which span of $R_o$ distances from about 1.47 inches (37 mm) to about 1.67 inches (42 mm), i.e., the range in which the operator expects to be measuring stresses in copper, and the mean and standard deviation of all fifteen readings were 0.9 KSI (6 Mpa)$\pm$0.7 KSI (5 Mpa). The X-ray information for each reading of the set of three, at each distance of $R_o$, was obtained in ten seconds, with a standard X-ray source, an unprecedented short time for collection of such information. The tolerance for variation in specimen-to-detector distance, i.e., the parameter designated $R_o$ herein, is unprecedented. The ability to tolerate such variations and provide good accuracy (i.e., 0.9 KSI compared with the true stress of zero) and precision (i.e., 0.7 KSI) in a very short time is a unique feature not present in any other similar combination of apparatus and procedure.

2.4 STRESS MEASUREMENT

With the stress measurement apparatus adjusted and calibrated, and with the quality of the calibration confirmed, internal (including residual) stress measurements on alpha copper alloy components can now be performed.

STEP 17: In this example the X-ray stress head shown in FIG. 1 was positioned over a small alpha brass electrical switch and the attitude of the head was adjusted so that the angle $\beta$ in FIG. 3 was 25°.

STEP 18: The distance between the stress head and switch, i.e., $R_o$, was then approximately set between 1.47 and 1.67 inches (37 and 42 mm).

STEP 19: The X-ray source was activated and the computer was prompted to determine the residual stress ($\sigma$) and $R_o$. Note: It was not necessary to read the crystallographic, elastic, and geometric parameters for the alpha brass, as well as the calibration coefficients, into the computer since that had previously been done during the confirmation. The resultant stress was 3.9 KSI (27 MPa) tensile and the $R_o$ was 1.50 inches (38.1 mm).

Stress measurements were continued for the rest of the day resulting in several tens of readings from electrical switch components with residual stresses ranging from 22.8 KSI (160 MPa) compression to 25.9 KSI (182 MPa) tensile and R ranging from 1.49 to 1.65 inches (37.8 to 41.9 mm).

Figure 5:
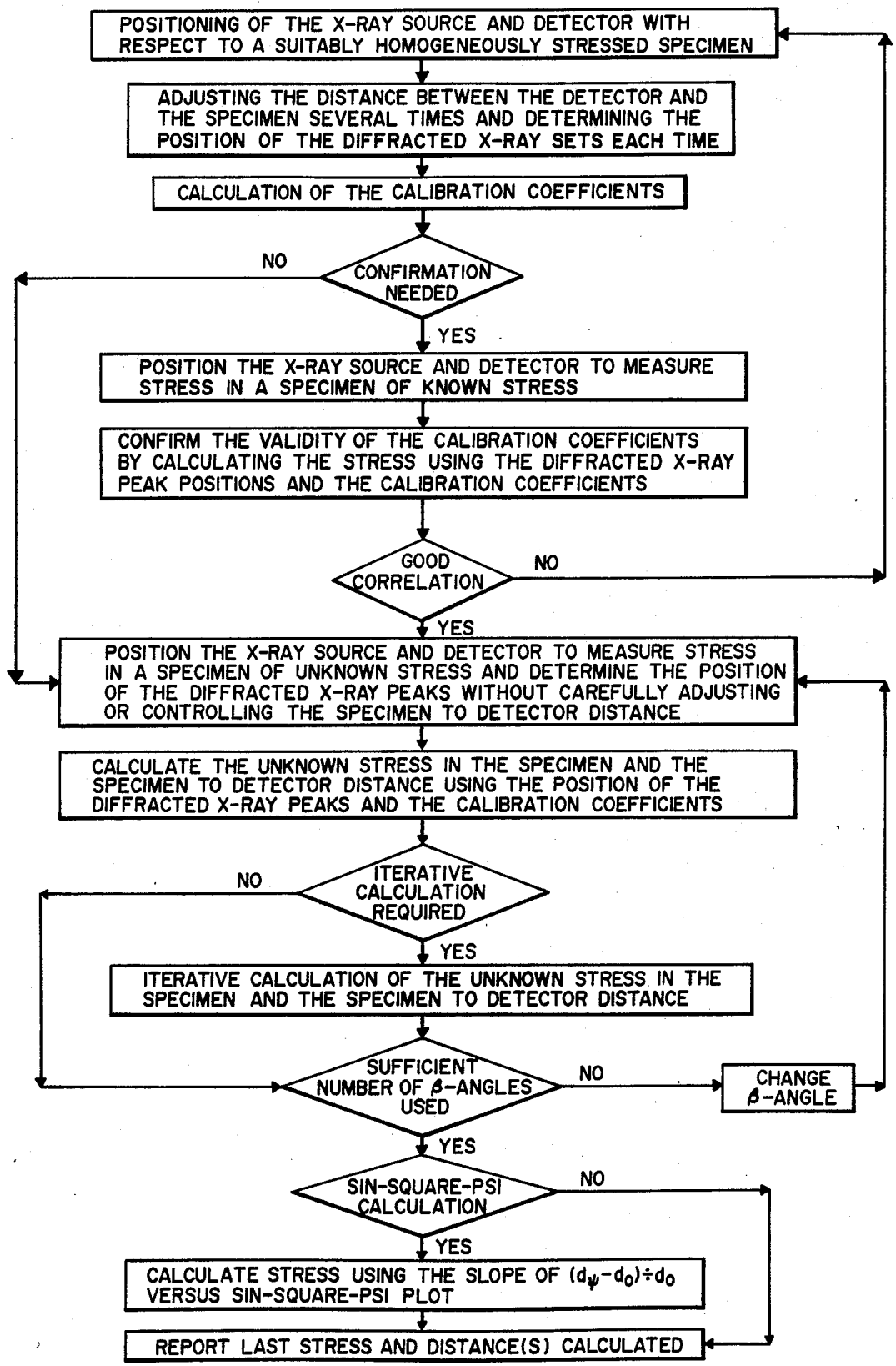
FIG. 5 is a flowchart of the method used in the present invention to calculate calibration coefficients.

Several of the above steps are shown in flowchart form in FIG. 5.

Although a position sensitive scintillation detector has been utilized in this invention, it is also possible that a position sensitive proportional detector or a position sensitive solid state detector be substituted to produce similar results. The invention has been described with a certain degree of particularity; however, it is understood that changes in device construction and method steps may be made without departing from the spirit of this invention.

I claim:

1. A method of obtaining calibration coefficients for residual internal stress measurements in polycrystalline specimens without accurate control or auxiliary measurements of the specimen to detector distance, $R_o$; the method comprising the steps of:
   (a) directing a monochromatic X-ray beam of known wavelength at a $\beta$ angle equal to zero at an area of homogeneous stress on a polycrystalline calibration specimen, in which $\beta$ equals the angle between the line of the incident X-ray beam and the normal to the specimen surface,
   (b) measuring the radial distance between reference locations on at least two radii of a skewed ellipse which is formed on a plane normal to the cone axis, for which the line of the incident X-ray beam is coincident with the axis of an elliptical cone of diffraction rays, and at least two diffracted sets of X-ray beams on the rays, and at least two diffracted sets of X-rays beams on the arc of the ellipse, where at least two of the diffracted sets of X-ray beams are opposite each other on the ellipse,
   (c) repeating step (b) at least twice, each time with a change in specimen to detector distance, $R_o$, with at least one of these distances being the idel $R_o$ distance which describes a circle along the circumference of which the X-ray detector surfaces are located,
   (d) calculating calibraction coefficients A, B, C, $S_{o1}$, and $S_{o2}$ wherein
   A,B,C = Calibration Coefficients as in the equation $$R = A \cdot L^2 + B \cdot L + C$$

wherein
   R = the distance between a reference location along a radial line of the skewed ellipse and the diffracted set of X-ray beams on the arc of the ellipse,
   L = the distance between a reference location along a second radial line of the skewed ellipse and the diffracted set of X-ray beams on the arc of the ellipse,
   $S_{o1}$ = a calibration coefficient representing the distance between the same reference location as for L along a radial line of the skewed ellipse and the spot representing the intersection of the line of the incident X-ray beam and the aforementioned plane normal to the cone axis, and
   $S_{o2}$ = a calibration coefficient representing the distance between the same reference location as for R along a second radial line of the skewed ellipse and the spot representing the intersection of the line of the incident X-ray beam and the aforementioned plane normal to the cone axis.

2. The method of claim 1 including the following additional steps following claim 1 step (d) to perform internal stress measurement by a single-$\beta$ angle technique,
   (a) directing a monochromatic X-ray beam of known wavelength at a $\beta$ angle not equal to zero at an area of a specimen of unknown stress,
   (b) measuring the radial distance between reference locations on two radii of a skewed ellipse, which correspond to the radii in claim 1 step (b) from which two diffracted sets of X-ray beams which were opposite each other on the arc of the ellipse were measured, and diffracted sets of X-ray beams on the arc of the ellipse,
   (c) calculating the stress in the unknown specimen and the specimen to detector distance, using the coefficients from claim 1 step (d) and the radial distances that are on opposite sides of the skewed ellipse from step (b) and the equations $$R_{o(1)} = \frac{L + R + (S_{o1} + S_{o2})}{2 \sin 2\eta_o}$$

and $$\sigma_{(1)} = \frac{E}{(1+\nu)} \frac{(R-L) - (L - AL^2 - BL - C)}{4 R_{o(1)} \sin^2 \theta_o \sin 2\beta}$$

wherein A, B, C, $S_{o1}$, $S_{o2}$, L, and R are as defined in claim 1 step (d) and
   $R_{o(1)}$ = the specimen to detector distance,
   $\sigma_{(1)}$ = the calculated stress in the area of the specimen,
   $\eta_o$ = the Bragg angle of an unstressed polycrystalline material of similar composition to the unknown specimen subtracted from ninety angular degrees, i.e., $90 - \theta_o$,
   E = Young's modulus,
   $\nu$ = Poisson's ratio, and
   $\theta_o$ = the Bragg angle for the unstressed polycrystalline material.

3. The method of claim 2 including the following additional steps following claim 2 step (c) to iteratively provide more accurate stress and specimen to detector values in the performance of the single-$\beta$ angle technique,
   (a) calculating a corrected $R_{o(n)}$ and $\sigma_{(n)}$ using the following equations, $$R_{o(n)} = \frac{L + R + (S_{o1} + S_{o2})}{2 \sin 2\eta_o} - \frac{L_{RERR} + R_{RERR}}{2 \sin 2\eta_o},$$

$$\sigma_n = \frac{E}{(1+\nu)} \frac{(R-L) - (L - AL^2 - BL - C)}{4 R_{o(1)} \sin^2 \theta_o \sin 2\beta}$$

wherein n > 1 and represents the number of iterative calculations performed, $$L_{RERR} = \frac{2\sigma_{(n-1)} R_{o(n-1)}}{(E/1+\nu)\cot \theta_o} \sin^2 \psi_L,$$

$$R_{RERR} = \frac{2\sigma_{(n-1)} R_{o(n-1)}}{(E/1+\nu)\cot \theta_o} \sin^2 \psi_R,$$

$$\psi_L = \beta - \eta_L, \psi_R = \beta + \eta_R,$$

$$\eta_L = \tfrac{1}{2} \text{Arc tan}[(L + S_{o1})/R_{o(n-1)}],$$

$$\eta_R = \tfrac{1}{2} \text{Arc tan}[(R + S_{o2})/R_{o(n-1)}], \text{ and}$$

(b) repeating the calculations of step a until $(\sigma_n - \sigma_{n-1}) \div \sigma_n$ is less than a given allowed error.

4. The method of claim 2 including the following additional steps following claim 2 step (c), to perform a multi-$\beta$ angle technique instead of a single-$\beta$ technique,
   (a) directing a monochromatic X-ray beam of known wavelength at a $\beta$ angle not equal to zero, nor the angle used in claim 2 step (a), and at the same area of a specimen of unknown stress as in claim 2 step (a), (b) repeating claim 2 steps (b) and (c) and calculating $\sin^2\Psi_L$, $\sin^2\Psi_R$, $d_L$, and $d_R$ values, for each $\beta$ angle using the following equations $$\Psi_L = \beta - \eta_L, \Psi_R = \beta + \eta_R,$$

$$\theta_L = 90° - \eta_L, \theta_R = 90° - \eta_R,$$

$$d_L = \lambda/2 \sin\theta_L, d_R = \lambda/2 \sin\theta_R,$$

wherein
$\eta_L = \frac{1}{2}$Arc tan $[(L+S_{o1})/R_{o(1)}]$,
$\eta_R = \frac{1}{2}$Arc tan $[(R+S_{o2})/R_{o(1)}]$,
and
$\lambda =$ the wavelength of the monochromatic radiation, (c) calculating the slope of a line of a graph of $(d_L-d_o)/d_o$ at various $\beta$ angles, and/or $(d_R-d_o)/d_o$ at various $\beta$ angles, plotted as a function of the corresponding $\sin^2\Psi$ values, and calculating the stress using the equation $$\sigma = \left(\frac{E}{1+\nu}\right) \times \text{(slope of the plot)},$$

wherein
$\sigma =$ calculated stress in the area of the specimen at which the X-ray beam was directed
and
$d_o = \lambda/2 \sin\theta_o$.

5. The method of claim 4 including the following additional steps after claim 4 step (b) and before claim 4 step (c) to iteratively provide more accurate stress and specimen to detector values in the performance of the multi-$\beta$ angle technique.

(a) calculating a corrected $R_{o(n)}$ and $\sigma_{(n)}$ at each $\beta$ angle using the following equations, $$R_{o(n)} = \frac{L + R + (S_{o1} + S_{o2})}{2\sin 2\eta_o} - \frac{L_{RERR} + R_{RERR}}{2\sin 2\eta_o},$$

$$\sigma_n = \frac{E}{(1+\nu)} \frac{(R-L) - (L - AL^2 - BL - C)}{4R_{o(1)}\sin^2\theta_o \sin 2\beta}$$

wherein $n > 1$ and represents the number of iterative calculations performed, and wherein $$L_{RERR} = \frac{2\sigma_{(n-1)}R_{o(n-1)}}{(E/1+\nu)\cot\theta_o} \sin^2\psi_L,$$

$$R_{RERR} = \frac{2\sigma_{(n-1)}R_{o(n-1)}}{(E/1+\nu)\cot\theta_o} \sin^2\psi_R,$$

$\psi_L = \beta - \eta_L, \psi_R = \beta - \eta_R,$ $\eta_L = \frac{1}{2}$ Arc tan$[(L + S_{o1})/R_{o(n-1)}]$, and $\eta_R = \frac{1}{2}$ Arc tan$[(R + S_{o2})/R_{o(n-1)}]$, (b) repeating the calculations of step (a) until $(\sigma_n - \sigma_{n-1}) \div \sigma_n$ is less than a given allowed error, and (c) calculating the slope and stress as in claim 4 step (c), using the last $d_L$ and $d_R$ values calculated from step (a) for each $\beta$ angle.

6. The method of claim 1 including the following additional steps to thereby confirm/not confirm the validity of coefficients A, B, C, $S_{o1}$, and $S_{o2}$ obtained from claim 1 step (d), (a) directing a monochromatic X-ray beam of known wavelength at a $\beta$ angle not equal to zero at an area of a specimen of known stress, (b) measuring the radial distance between reference locations on two radii of a skewed ellipse, which correspond to the radii in claim 1 step (b) from which two diffracted sets of X-ray beams which were opposite each other on the arc of the ellipse were measured, and diffracted sets of X-ray beams on the arc of the ellipse, (c) calculating the stress in the known specimen and the specimen to detector distance, using the coefficients from claim 1 step (d) and the radial distances that are an opposite sides of the skewed ellipse from claim 1 step (b) and the equations $$R_{o(1)} = \frac{L + R + (S_{o1} + S_{o2})}{2\sin 2\eta_o}$$

and $$\sigma_{(1)} = \frac{E}{(1+\nu)} \frac{(R-L) - (L - AL^2 - BL - C)}{4R_{o(1)}\sin^2\theta_o \sin 2\beta}$$

wherein A, B, C, $S_{o1}$, $S_{o2}$, L, and R are as defined in claim 1 step (d) and
$R_{o(1)} =$ the specimen to detector distance,
$\sigma_{(1)} =$ the calculated stress in the area of the specimen,
$\eta_o =$ the Bragg angle of an unstressed polycrystalline material of similar composition to the unknown specimen substracted from ninety angular degrees, i.e., $90 - \theta_o$,
E = Young's modulus,
$\nu =$ Poisson's ratio,
$\theta_o =$ the Bragg angle for the unstressed polycrystalline material, and (d) comparing the calculated stress from step (c) with the known stress in the specimen to confirm/not confirm the validity of the coefficients obtained from claim 1 step (d).

7. The method of claim 6 in which the known polycrystalline specimen is a powder of zero stress.

8. The method of claim 1 in which step (b) is carried out by means of a single X-ray detector having at least two channels.

9. The method of claim 8 wherein said X-ray detector is a position sensitive detector.

10. The method of claim 8 wherein said X-ray detector is a position sensitive proportional detector.

11. The method of claim 8 wherein said X-ray detector is a position sensitive scintillation detector.

12. The method of claim 11 wherein said detector has light transmission means in the form of a pair of elongate fiber optic bundles each terminating at one end in image-receiving surfaces located in predetermined angular ranges in relation to the incident X-ray beam, said image receiving surfaces being of such size and shape when placed in close proximity to a sample so that the diffracted X-ray beam impinges upon these surfaces to intercept at least two diffracted beams, on each side of the incident beam; a scintillating phosphor coating on said image-receiving surfaces, said phosphor being responsive to X-ray radiation and operative when so activated to reproduce an image of the X-rays in the visible spectrum; image intensification means located adjacent to the other end of said fiber optic bundle operative to receive the visible light image transmitted thereto and increase the intensity thereof; an array of photosensitive diodes and associated precharged capacitors arranged in face-to-face relationship to the intensified image, said photodiodes being responsive to visible light and operative when thus activated to store an electronic signal determined by having a functional relationship to the visible light impinging thereon; and signal processing means which collects and stores data from the photosensitive arrays and displays the signal derived therefrom so as to reveal the position and intensity of the diffracted beam.

* * * * *